US011260037B2

(12) United States Patent
Chu et al.

(10) Patent No.: US 11,260,037 B2
(45) Date of Patent: Mar. 1, 2022

(54) OAT FRACTIONS WITH ENHANCED AVENANTHRAMIDE CONCENTRATION AND METHODS OF MAKING

(71) Applicant: THE QUAKER OATS COMPANY, Chicago, IL (US)

(72) Inventors: YiFang Chu, Glenview, IL (US); Jodee Johnson, Huntley, IL (US); Marianne O'Shea, Chicago, IL (US)

(73) Assignee: The Quaker Oats Company, Chicago, IL (US)

( * ) Notice: Subject to any disclaimer, the term of this patent is extended or adjusted under 35 U.S.C. 154(b) by 124 days.

(21) Appl. No.: 16/407,827

(22) Filed: May 9, 2019

(65) Prior Publication Data
US 2019/0262296 A1 Aug. 29, 2019

Related U.S. Application Data

(62) Division of application No. 14/508,580, filed on Oct. 7, 2014, now Pat. No. 10,335,383.

(51) Int. Cl.
*A61K 36/899* (2006.01)
*A61K 36/00* (2006.01)
*A61K 31/196* (2006.01)
*A23L 7/10* (2016.01)

(52) U.S. Cl.
CPC ............ *A61K 31/196* (2013.01); *A23L 7/115* (2016.08); *A23L 7/197* (2016.08); *A23L 7/198* (2016.08); *A61K 36/899* (2013.01); *A23V 2002/00* (2013.01)

(58) Field of Classification Search
None
See application file for complete search history.

(56) References Cited

U.S. PATENT DOCUMENTS

2012/0082740 A1  4/2012  Collins
2013/0209610 A1* 8/2013  Carder ................. A23L 7/107
                                                    426/28

OTHER PUBLICATIONS

Office Action dated Sep. 16, 2020, in Canadian Application No. 2963932.
Hao, Liu et al: "Using Fourier Transform near Infrared Spectroscopy to Estimate the Nutritional Value in Whole and Milled Naked Oats", Journal of Near Infrared Spectroscopy, vol. 22, No. 2, Jan. 1, 2014 (Jan. 1, 2014), pp. 93-101, XP055453006.
Dimberg, Lena H. et al.: "Quantitative Analysis of Oat Avenanthramides", Healthgrain Methods: Analysis of Bioactive Components in Small Grain Cereals, Dec. 31, 2009, Elsevier, pp. 113-127, XP055453039.
Ocean Optics, "NIRQuest512-1 9 and Vivo Flour Transmission Measurements.xlsx," Aug. 5, 2014, 2 pages.
Serranti, et al., "Classification of Oat and Groat Kernels using NIR Hyperspectral Imaging," Talanta, vol. 103, Jan. 15, 2013, pp. 276-284.
Doehlert, et al., Douglas C., "Oat Grain Density Measurement by Sand Displacement and Analysis of Physical Components of Test Weight," Cereal Chem., vol. 85(5):654-659, 2008, 6 pages.
Akhalaya, M.Ya., et al., "Molecular Action Mechanisms of Solar Infrared Radiation and Heat on Human Skin," Ageing Research Reviews, Elsevier B.V., Apr. 15, 2014, 11 pages.
Ruschy, David L., "Seasonal Variation in Daily Temperature Ranges," Soil Science Department, University of Minnesota, St. Paul, Minnesota, Dec. 1991, Journal of Climate, vol. 4, 1211-1216, 6 pages.
Landsberg, H. E., "Solar Radiation at the Earth's Surface," Solar Energy, vol. 5, Issue 3, Sep. 1961, 95-98, 4 pages.
Itaca, "Part 2: Solar Energy Reaching The Earth's Surface," www.itacanet.org/the-sun-as-a-source-of-energy/part-2-solar-energy-reaching-the-earths-surface/, Jun. 22, 2014, 11 pages.
Fondriest Environmental, Inc. "Solar Radiation and Photosynthically Active Radiation." Fundamentals of Environmental Measurements. Mar. 21, 2014. Web. < http://www.fondriest.com/environmental-measurements/parameters/weather/solar-radiation/ > 14 pages.
Doehlert, Douglas C., et al. "Evaluation of oat kernel size uniformity." Crop Science, vol. 44, No. 4, 2004, p. 1178+. Academic OneFile, Accessed Sep. 22, 2017.
Lee et al, "Effect of far-infrared radiation and heat treatment on the antioxidant activity of water extracts from peanut hulls," Food Chemistry 94 (2006) pp. 489-493, abstract.
Skoglund, "Phenolic Compounds in Oats, Effects of Steeping, Germination, and Related Enzymes," Doctoral thesis, Swedish University of Agricultural Sciences Uppsala, 2008, p. 19, lines 4,5,7.
Wanyo et al, "Effects of different treatments on the antioxidant properties and phenolic compounds of rice bran and rice husk," Food Chemistry 157 (2014) pp. 457-463, Feb. 25, 2014, abstract.

(Continued)

*Primary Examiner* — Michael Barker
*Assistant Examiner* — Randall O Winston
(74) *Attorney, Agent, or Firm* — Barnes & Thornburg LLP; G. Peter Nichols

(57) ABSTRACT

Exemplary embodiments provide oat fractions, and methods of producing the oat fractions, of the species *Avena Sativa* that has a concentration of total Avenanthramides that is from about 2 to about 25 wt. %, and up to about 30 wt. % or more, higher than the concentration before treatment with infrared energy. The higher concentration is achieved without treatment with enzymes or exposure to fungal agents to increase the concentration of total Avenanthramides. Instead, the enhanced concentration of Avenanthramides is achieved through exposure to infrared energy for a selected period of time.

19 Claims, 3 Drawing Sheets

(56) References Cited

OTHER PUBLICATIONS

Examination Report dated Aug. 4, 2020 in European Application No. 15849047.4.
Lee et al: "Effect of Far-Infrared Radiation on the Antioxidant Activity of Rice Hulls", Journal of Agricultural and Food Chemistry, vol. 51, No. 15, Jan. 1, 2003, p. 4400-4403.

* cited by examiner

OAT FRACTIONS WITH ENHANCED AVENANTHRAMIDE CONCENTRATION AND METHODS OF MAKING

CROSS-REFERENCE TO RELATED APPLICATIONS

The present application is a divisional application of and claims priority to U.S. Nonprovisional patent application Ser. No. 14/508,580, entitled "Oat Fractions with Enhanced Avenanthramide Concentration and Methods of Making," filed on Oct. 7, 2014, and published as US 2016/0095335 A1 on Apr. 7, 2016, which application and publication are herein incorporated by reference in their entirety as examples.

BACKGROUND OF THE INVENTION

Field of the Technology

The technology relates to the area of grains, and more particularly to the area of treatment of the grains to enhance the concentration of particular grain components, namely, Avenanthramides.

Description of the Related Art

Oatmeal has been a staple of the human diet for centuries, and in more recent years emphasis has been placed on its potential health benefits. Avenanthramides are phenolic antioxidants uniquely found in oats. More than 30 congeners have been characterized since they were first isolated in the 1980s, with the most abundant being 2p, 2f and 2c. These polyphenols demonstrate potent antioxidant, anti-inflammatory and anti-atherosclerotic properties that may be beneficial for people with chronic inflammatory diseases, allergies and cardiovascular disease. The benefits of Avenanthramides have also been documented outside of the food industry. One of the main reasons colloidal oatmeal is used in the skin care product line Aveeno™ (sold by Johnson & Johnson) is because of the demonstrated anti-inflammatory activities of Avenanthramides on skin. Tranilast, an Avenanthramide analogue, is a drug used to treat allergic disorders such as asthma, allergic rhinitis and atopic dermatitis.

To benefit human health, a sufficient amount of an Avenanthramide must be orally ingested. A 1999 human study at Tufts University confirmed that Avenanthramides are bioavailable and remain bioactive after ingestion, with maximum total plasma Avenanthramide concentrations of 168 and 560 nM, after 60 and 120 mg consumption, respectively. A more recent study from the University of Minnesota showed that 8 weeks of Avenanthramide consumption at doses as low as 0.4-9.2 mg/day increases plasma total antioxidant activity, and affects several antioxidant and anti-inflammatory parameters in a dose-dependent manner. These results are possibly due to the accumulation of the Avenanthramides in various tissues and organs associated with long-term consumption. Therefore, increasing the Avenanthramide content of oat fractions may enhance the health benefits of oatmeal and of other edible food products that include oat fractions as an ingredient.

Many studies have investigated ways of increasing Avenanthramide content in oats. Because the concentration of Avenanthramides varies among the different genetic variations of oats, and because infection with the fungus crown rust (*Puccinia coronata*) increases the concentration of Avenanthramides, selective breeding and molecular mimics of fungal infections have been used to enhance the Avenanthramide content in oats. An industrial process called "false malting," in which oat grains are conventionally malted, but do not germinate, has also been used to increase the Avenanthramide content.

Like other phenolic compounds, most of the Avenanthramides found in oat grains are complex insoluble esters bound with other macromolecules, such as polysaccharides, proteins and cell walls, and are not biologically available. Breaking these bonds liberates the Avenanthramides and enables them to be absorbed by the body, which is essential for maximizing the nutritional value of the oat products. Enzymatic digestion with *Aspergillus* ferulic acid esterase and *Trichoderma* xylanases has been shown to release hydroxycinnamic acids, a group of minor phenolic acids, from oat hulls. However, enzymatic methods are complex and using them in commercial settings may not be practically useful. Additionally, separating out the enzymes after a reaction can be costly, and high temperatures during commercial oat processing could deactivate enzyme activities. Furthermore, Avenanthramides are biphenolic compounds that differ structurally from phenolic acids, which only have one phenolic ring. To date, it appears that no study has been shown to release Avenanthramides from the oat matrix using non-enzymatic methods.

SUMMARY

The following is a summary of some aspects and exemplary embodiments of the present technology, of which a more detailed explanation is provided under the Detailed Description section, here below.

An exemplary embodiment provides oat fractions of the species *Avena Sativa* that has a higher concentration of Avenanthramides than the concentrations that occur naturally in the species. The higher concentrations are achieved without treatment with enzymes or exposure to fungal agents. Instead, the enhanced concentrations of the Avenanthramides are achieved through exposure of an oat fraction to infrared energy for a selected period of time. The selected time period corresponds to a desired level of exposure to infrared energy per kg of the oat fraction that will produce the enhanced concentration sought. The oat fraction treated with infrared energy may be edible or inedible. Post-infrared treatment, the treated oat fraction, whether edible or inedible, may be processed to extract Avenanthramides to be applied to other uses, for example, in nutritional supplements, or as a food additive. An edible treated oat fraction may be made available for human or animal consumption, as a cereal or in other foodstuffs.

Another exemplary embodiment provides a food product that includes an oat fraction, wherein the oat fraction is derived from the species *Avena Sativa*, and wherein the oat fraction has a concentration of total Avenanthramides ranging from about 2 to about 25 wt. % higher than before treatment with infrared energy. The higher Avenanthramide concentrations are achieved without treatment with enzymes or exposure of the oat fraction to fungal agents to increase the Avenanthramides concentrations. The food product may be a shelf-stable product, or may be a refrigerated food product.

A further exemplary embodiment provides a method of increasing the concentration of Avenanthramides of an oat fraction, without treatment of the oat fraction with enzymes and without exposure of the oat fraction to a fungus. The method includes the step of: exposing the oat fraction to infrared energy for a period of time sufficient to increase the concentration of Avenanthramides of the oat fraction.

BRIEF DESCRIPTION OF THE DRAWINGS

The foregoing aspects and many of the attendant advantages, of the present technology will become more readily appreciated by reference to the following Detailed Description, when taken in conjunction with the accompanying simplified drawings of exemplary embodiments. The drawings, briefly described here below, are not to scale, are presented for ease of explanation and do not limit the scope of the inventions recited in the accompanying patent claims.

DETAILED DESCRIPTION

Figure 1:
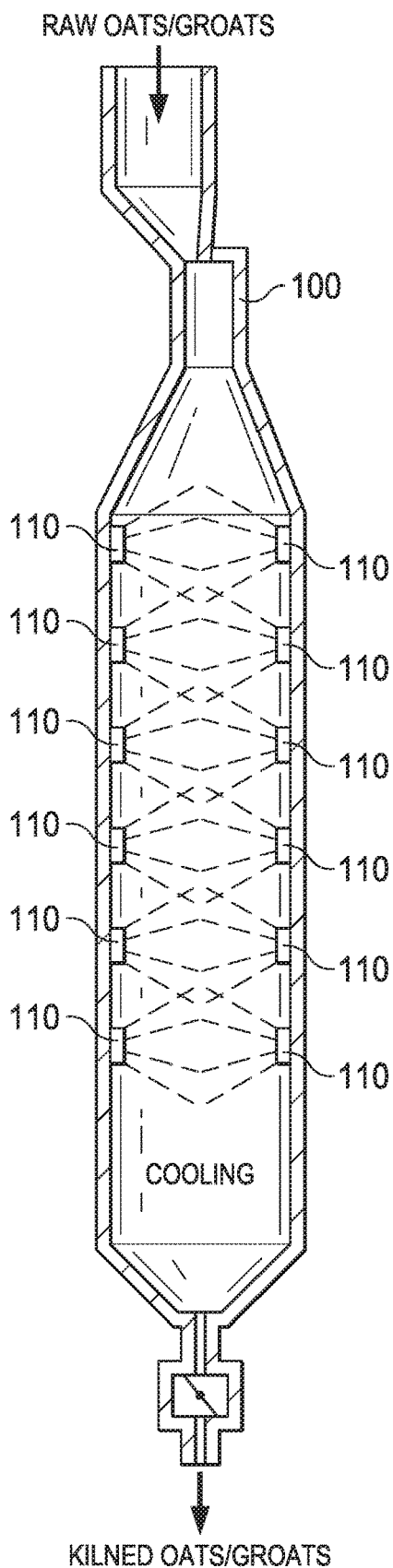
FIG. 1 is a schematic representation illustrating an exemplary method and apparatus in wherein the oat fractions are treated with infrared energy while undergoing kilning.

The following detailed description is exemplary in nature facilitating an understanding of the inventions embodied in the appended patent claims. This detailed description is not intended to, and does not limit the inventions to the described exemplary embodiments, or the application and uses of the exemplary embodiments. Furthermore, there is no intention to be bound by any express or implied theory presented in the preceding background, summary or the following detailed description.

As a preliminary matter, infrared light has a longer wavelength and lower frequency than visible light and is divided into near-infrared (high-energy, 0.75-1.5 μm wavelength), mid-infrared (mid-energy, 1.5-4 μm wavelength) and far-infrared (low-energy, 4-1000 μm wavelength) regions. Chemical compounds absorb particular frequencies of infrared energy based on their molecular structure and the energy is transferred to compounds for bond vibrations. Treatment with infrared energy is not a commonly used method for breaking chemical bonds because its energy content is generally considered to be relatively low.

In the exemplary embodiments and the patent claims, below, reference is made to the concentration of Avenanthramide or Avenanthramides. An exemplary method of measuring the concentration of an Avenanthramide, which can be selected from several Avenanthramide congener compounds, designated for example as 2c, 2p, 2f, and 5p, etc., includes the use of reverse-phase high-performance liquid chromatography (HPLC) analysis. In this procedure, the peaks corresponding to the Avenanthramide congener compounds 2c, 2p, 2f and 5p, such as occur in oat flour, trichomes, and hulls, may be quantified by comparing the obtained peak areas to those of standard curves. From this analysis the concentration of an Avenanthramide congener (in mg/kg) can readily be determined. The HPLC method of analysis detects free forms of Avenanthramide congeners. Accordingly, as used herein, the term "concentration of Avenanthramides" refers to the concentration of the free form of the Avenanthramide congeners, such as exemplary congeners 2c, 2f, 2p, and/or 5p, present in the oat fraction. The term "total Avenanthramide concentration" refers to the sum of the measured concentrations of Avenanthramide congeners present in the oat fraction. Unless otherwise indicated, all reference to a percentage increase in Avenanthramide concentration, irrespective of which congener, refers to a weight percent ("wt. %") increase.

As detailed below, the treatment methodology and the results of enhancing the concentration of Avenanthramides are applicable to "oat fractions." An oat fraction may be selected from oat flour, oat trichomes and oat hulls.

It is theorized, without being bound, that free forms of the various Avenanthramide congeners may have different advantages in terms of biological functions. For example, Avenanthramide 2c may have the highest antioxidant activity in vitro and Avenanthramide 2p may possess the highest bioavailability after consumption in vivo. Avenanthramide 2f may have the greatest proportional increase in bioavailability with larger doses. Using infrared treatment to increase the Avenanthramide content in oat fractions may affect the bioavailability and antioxidant activity of the Avenanthramides in each oat fraction differently. For example, for oat flour, infrared energy may increase both bioavailability and antioxidant activity by a similar proportion, whereas for trichomes it may enhance antioxidant activity more than bioavailability.

In exemplary embodiments, oat fractions treated to enhance the concentration of Avenanthramides retain the enhanced Avenanthramides concentration during the normally expected shelf-life of the oat fractions, whether as oat fractions, or in the form of a food product that includes other ingredients. These products that include other ingredients include, but are not limited to granola, breakfast bars, and breakfast cereals. In exemplary embodiments of food products that combine at least one oat fraction with ingredients that require refrigeration, the oat fraction also retains its enhanced Avenanthramides concentration for the shelf-life of the product.

In accordance with an exemplary embodiment of methods of enhancing the concentration of Avenanthramides in an oat fraction, the oat fraction is are treated with infrared energy for a time sufficient to increase the concentration of total Avenanthramides by from about 1 to about 70 wt. %, or about 5 to about 70 wt. %, as compared to the oat fraction that was charged to the infrared treatment process, which had not been treated with infrared energy or another treatment to enhance the concentration of Avenanthramide.

In another embodiment, the oat fraction is treated with infrared energy for a time sufficient to increase the concentration of total Avenanthramides by from about 5 to about 20 wt. % as compared to the oat fractions charged to the treating process, which had not been treated with infrared energy or another treatment to enhance the concentration of Avenanthramides. In yet another exemplary embodiment, the oat fraction is treated with infrared energy for a time sufficient to increase the concentration of total Avenanthramides by from about 10 to about 15%, as compared to the oat fractions charged to the treating process, which had not been treated with infrared energy or another treatment to enhance the concentration of Avenanthramides. In a further exemplary embodiment, the oat fractions are treated with infrared energy for a time sufficient to increase the concentration of total Avenanthramides by from about 5 to about 50% as compared to the oat fractions charged to the treating process, which had not been treated with infrared energy or another treatment to enhance the concentration of Avenanthramides.

In an exemplary embodiment, the oat fraction is treated with a quantum of infrared energy within a range of Kilojoules per mass (grams) of the oat fraction. In practice, this corresponds to treatment for a period of time to provide the exposure to the amount of infrared energy necessary to produce a desired level of increase in Avenanthramide concentration. In general, it has been found that the concentration of total Avenanthramides increases with increasing exposure to infrared energy, until at some point the concentration begins to decrease as the energy input increases. As a result, in exemplary embodiments that seek to maximize the concentration of Avenanthramides, there is an optimum range of time of exposure of the oat fractions to the infrared energy. It has been found that the duration of exposure to maximize the concentration of Avenanthramides in oat flour, trichomes and hulls, differs. Further, it has been found that the treatment with infrared energy does not increase each of the Avenanthramide congeners by the same amount; some are more responsive to treatment than others.

With regard to the observed decrease of Avenanthramide concentration with excessive exposure to infrared energy, it is theorized without being bound that excessively long exposure times may degrade the bound and the free Avenanthramide congeners. This may explain the reduction in some detected free Avenanthramide congeners after excessively long exposure to infrared energy. The variation in the optimal treatment duration for maximizing Avenanthramides content may be explained by different matrix effects that may occur in oat flour, trichomes, and hulls, due to the differing compositions of these oat fractions. The major components of oat flour include starch and other macromolecules, such as proteins; while trichomes primarily include insoluble polysaccharides; and hulls are mainly comprised of cellulose and hemicellulose.

The infrared treatment of oats or oat fractions may take place in the equipment and processing steps usually employed in the processing of oats, or may take place in an additional step to the usually employed processing. For example, the treatment may take place while oats are being transferred to or from storage hoppers, or inside these hoppers. Additionally, or alternatively, the infrared treatment of the oats may take place during the process of kilning the oats. As illustrated in FIG. 1, the kiln 100, represented generically, may be supplied with a plurality of internal infrared emitters 110 that irradiate the oat fractions during the kilning process. The infrared emitters 110 may be located in an array and controlled with timers (not shown) so that the extent and duration of exposure to the infrared energy is controlled to either maximize Avenanthramides concentration, or to achieve another concentration that yet enhances the Avenanthramides concentration as compared to the base level of the oat fractions. While application of heat does not by itself enhance Avenanthramides content, the process of treating the oat fractions with infrared energy generates heat. Accordingly, the process of treating the oat fractions may advantageously be applied during kilning of the oat fractions.

Further additionally or alternatively, the treatment with infrared energy treatment may take place during rolling or flaking when the oats are pressed between opposed rollers.

The treatment with infrared energy may take place wherever it is convenient to do so for the oat fraction(s) wherein it is desired to enhance the Avenanthramide concentration. In another exemplary embodiment a separate step may be added to the typical processing of oats wherein during this step the oats or oat fraction(s) under consideration are subjected to Infrared energy for a time sufficient to achieve a desired increase in the concentrations of Avenanthramides. Thus, infrared treatment is not limited to being carried out during kilning or flaking: in some cases, the oat fraction(s) may advantageously be diverted to a separate processing step to carry out the infrared treatment. The oat fraction may be treated prior to packaging as a product, or may also be treated in transit from one processing step to another in the overall oat processing system.

Oat hulls that are often regarded as a "waste product" of low value but as a consequence of infrared treatment to increase the Avenanthramide concentration, as described herein, hulls may have enhanced value as a raw material source of Avenanthramides.

In general, for convenience, in a manufacturing/processing plant environment the extent of exposure of the selected oat fraction(s) to infrared energy may be measured in time. For example, in a process operating environment, exposure might be timed at 15, 20, 30 minutes, or more, to achieve the desired concentration of an Avenanthramide congener concentration or the concentration of total Avenanthramides. However, it will be readily appreciated that the increase in Avenanthramide concentration is dependent upon the extent of exposure to and absorption of infrared energy by the oat fraction being treated. The amount of energy the oat fraction is exposed to or absorbs is measured in Kilojoules per gram (KJ/g). Exemplary FIGS. 2 and 3, respectively, illustrate graphically the incremental change in concentration of total Avenanthramides (percent) with increasing exposure to infrared energy; and the incremental change in concentration of total Avenanthramides with (calculated) increasing absorption of infrared energy for each of: oat flour (curve A), oat trichomes (curve B), and oat hulls (curve C). As can be seen from FIG. 2, in general, for almost all oat fractions, the concentration of total Avenanthramides tends to increase with increasing exposure (and absorption) of infrared energy. The oat fractions were not exposed to any other treatment to increase the concentration of total Avenanthramides.

Figure 2:
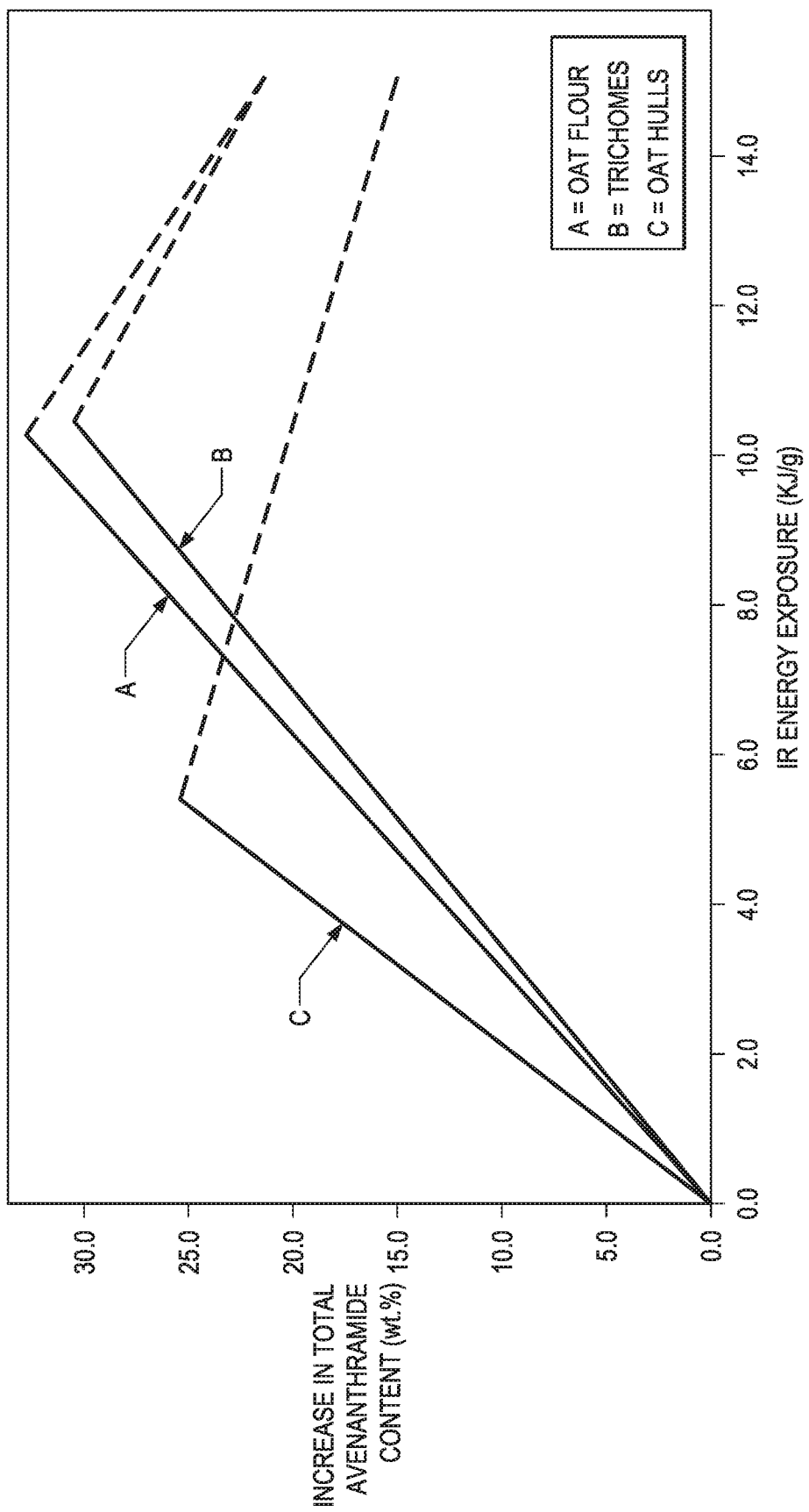
FIG. 2 is an exemplary graphic illustration of increase in Avenanthramide concentration (y-axis) with increasing exposure to infrared energy (KJ/Kg) (x-axis).

Regarding exemplary FIG. 2, more specifically, it can be seen that the concentration of total Avenanthramides (i.e. sum of all congeners) in oat flour fractions depicted by curve A increases up to about 30 wt. % above the base level in the untreated oat flour as infrared energy exposure increases up to about 10 KJ/g. Beyond the 10 KJ/g energy exposure, as depicted by the extrapolated broken line portion of the curve A, the concentration of total Avenanthramides may decrease slightly. However, it remains consistently above the level of the concentration in the oat flour prior to exposure to infrared energy. Similarly, for the oat trichomes fraction, depicted as curve B, the concentration of total Avenanthramides increases steadily up to about 28 wt. % above the base level in the untreated oat trichomes, achieved at about 10 KJ/g. Beyond the 10 KJ/g energy exposure, as depicted by the extrapolated broken line portion of the curve B, the concentration of total Avenanthramides may decrease slightly. However, it remains consistently above the level of the concentration in the oat trichomes prior to exposure to infrared energy. Similarly, for the oat hulls fraction, depicted as curve C, the concentration of total Avenanthramides increases steadily up to about 25 wt. % above the base level in the untreated oat hulls, achieved at about 5 KJ/g of infrared energy exposure. Beyond the 5 KJ/g energy exposure, as depicted by the extrapolated broken line portion of the curve C, the concentration of total Avenanthramides may decrease slightly. However, it remains consistently above the level of the concentration in the oat hulls prior to exposure to infrared energy. In this instance, only about 50% of the energy was absorbed.

Exposure to infrared energy may be correlated to absorption of the energy, which is dependent upon several factors, including, for example, the propensity of the substance being exposed to infrared energy to absorb the infrared energy. In practice the correlation may have to done on a case by case basis taking into account the specific parameters that apply in the particular circumstances. However, with regard to the oat fractions, comparing FIGS. 2 and 3, it becomes clear that the pattern of consistent increase in the concentration of total Avenanthramides is repeated, but is "shifted along the x-axis" due to the difference between the energy to which the oat fraction is exposed versus the energy it absorbed. Not all energy is absorbed; some is reflected or otherwise lost.

Figure 3:
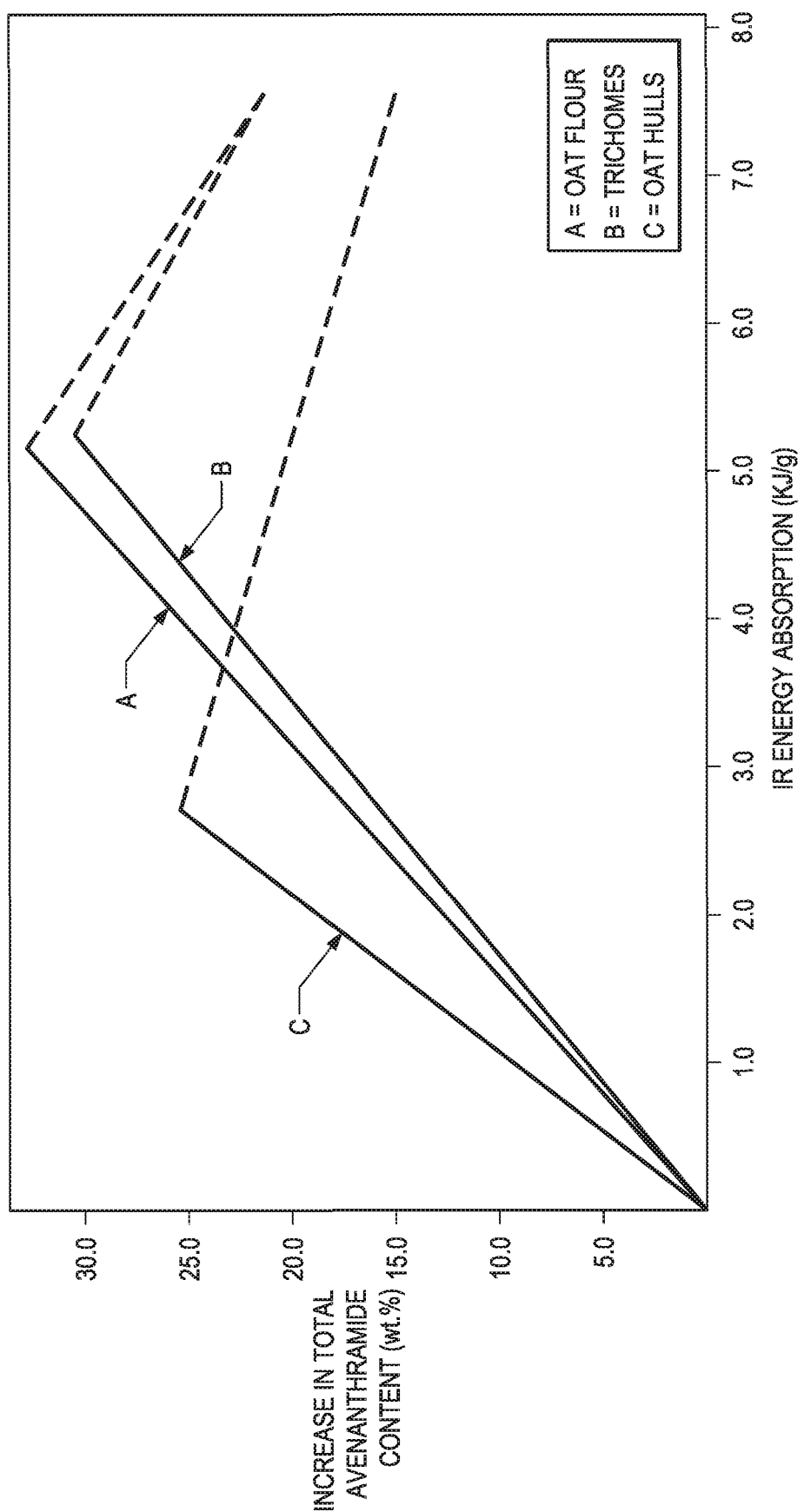
FIG. 3 is a representational and exemplary graphic illustration of increase in Avenanthramide concentration (y-axis) with increasing absorption of infrared energy (KJ/Kg) (x-axis), based on an assumed percent absorption.

Regarding representational and exemplary FIG. 3, more specifically, it can be seen that the concentration of total Avenanthramides (i.e. sum of all congeners) in oat flour fractions depicted by curve A increases up to about 30 wt. % above the base level in the untreated oat flour as infrared energy absorption increases up to about 4.2 KJ/g. Beyond the 4.2 KJ/g energy absorption, as depicted by the extrapolated broken line portion of the curve A, the concentration of total Avenanthramides may decrease slightly. However, it remains consistently above the level of the concentration in the oat flour prior to absorption to infrared energy. Similarly, for the oat trichomes fraction, depicted as curve B, the concentration of total Avenanthramides increases steadily up to about 28 wt. % above the base level in the untreated oat trichomes, achieved at about 4.2 KJ/g. Beyond the 4.2 KJ/g energy absorption, as depicted by the extrapolated broken line portion of the curve B, the concentration of total Avenanthramides may decrease slightly. However, it remains consistently above the level of the concentration in the oat trichomes prior to exposure to and absorption of infrared energy. Similarly, for the oat hulls fraction, depicted as curve C, the concentration of total Avenanthramides increases steadily up to about 25 wt. % above the base level in the untreated oat hulls, achieved at about 2 KJ/g of infrared energy absorption. Beyond the 2 KJ/g energy absorption, as depicted by the extrapolated broken line portion of the curve C, the concentration of total Avenanthramides may decrease slightly. However, it remains consistently above the level of the concentration in the oat hulls prior to exposure to and absorption of infrared energy.

In an exemplary embodiment, after treating oat flour with infrared energy for about 60 minutes (about 10 KJ/g exposure), the concentration of total Avenanthramides increased by about 25 wt. %, and the concentration of congeners 2c, 2p and 2f increased by about 20 wt. %, 25 wt. % and 25 wt. %, each, respectively. Continued treatment to about 90 minutes (about 15 KJ/g exposure) decreased the concentrations to less than achieved at the about 60 minute mark. Thus, the total Avenanthramide concentration after about 90 minutes was reduced to about a 16 wt. % increase over the base level prior to any infrared energy exposure.

In an exemplary embodiment, infrared energy significantly increased the concentration of total Avenanthramides in oat trichomes by about 25 wt. % after about 60 minutes (about 10 KJ/g exposure) of treatment. Continued treatment decreased the concentration of total Avenanthramides to about a 15 wt. % increase over the base level, after about 90 total minutes (about 15 KJ/g exposure) of treatment. In an exemplary embodiment, the concentrations of the 2c, 2p, 2f and 5p Avenanthramide congeners also increased over the base level at these treatment intervals. More particularly, in the exemplary embodiment, congener 2c increased by about 45 wt. % after about 60 minutes, congener 2p increases by about 20 wt. % after about 60 minutes; congener 2f increases by 15 wt. % after about 60 minutes; and congener 5p increases to about a 70 wt. % gain after about 60 minutes.

In an exemplary embodiment treating oat hulls with infrared energy for about 30 minutes (about 5 KJ/g exposure), total Avenanthramides concentration increased by about 20 wt. %, and the concentration of congeners 2f increased by about 20 wt. %, while 2p increased by about 15 wt. %.

In an exemplary embodiment, the concentration of total Avenanthramides in oat flour is increased, relative to oat flour untreated for Avenanthramide concentration enhancement, by greater than about 15 wt. %; and in another exemplary embodiment, the increase is greater than about 30 wt. %. And, in a further exemplary embodiment from about 5 to about 25 wt. %. In a yet further exemplary embodiment, the concentration of Avenanthramides in the oat flour is increased, relative to oat flour untreated for Avenanthramide concentration enhancement, by from about 10 to about 20 wt. %.

In an exemplary embodiment, the concentration of Avenanthramides in the oat trichomes is increased, relative to oat trichomes untreated for Avenanthramide concentration enhancement, by greater than 10 wt. %, or by from about 15 to about 70 wt. %. In another exemplary embodiment, the concentration of Avenanthramides in the oat trichomes is increased, relative to oat trichomes untreated for Avenanthramide concentration enhancement, by from about 25 to about 70 wt. %.

In an exemplary embodiment, the concentration of Avenanthramides in the oat hulls is increased, relative to oat hulls untreated for Avenanthramide concentration enhancement, by greater than 2 wt. %, or by from about 2 to about 20 wt. %. In another exemplary embodiment, the concentration of Avenanthramides in the oat hulls is increased, relative to oat hulls untreated for Avenanthramide concentration enhancement, by from about 5 to about 20 wt. %.

In an exemplary embodiment, the concentration of Avenanthramides congener 2c is increased, relative to the oat product untreated for Avenanthramide concentration enhancement, by at least about 45 wt. % or by from about 10 to about 45 wt. %. In an exemplary embodiment, the concentration of Avenanthramide congener 2f is increased, relative to the oat product untreated for Avenanthramide concentration enhancement, by from about 1 to about 25 wt. %. In an exemplary embodiment, the concentration of Avenanthramide congener 2p is increased, relative to the oat product untreated for Avenanthramides enhancement, by from about 5 to about 25 wt. %. In an exemplary embodiment, the concentration of Avenanthramide congener 5p is increased, relative to the oat product untreated for Avenanthramides enhancement, by from about 10 to about 70 wt. %.

While at least one exemplary embodiment has been presented in the foregoing detailed description section, it should be appreciated that many variations exist. It should also be appreciated that the exemplary embodiments are only examples, and are not intended to limit the scope, applicability, or configuration of the claimed inventions in any way. Rather, the foregoing detailed description provides a convenient road map for those of ordinary skill in the art to implement exemplary embodiments. It should be understood that various changes can be made in the function and arrangement of elements described herein without departing from the scope of the patent claims listed below, including the legal equivalents of these patent claims.

The invention claimed is:

1. A method of increasing an Avenanthramide concentration in an oat fraction, without treatment of the oat fraction with enzymes and without exposure of the oat fraction to a fungus, the method comprising the steps of:

selecting an oat fraction derived from the species *Avena Sativa* having a natural Avenanthramide concentration; and exposing the selected oat fraction to a selected quantum of infrared energy for a sufficient amount of time such that an Avenanthramide concentration in the exposed selected oat fraction is greater than the natural Avenanthramide concentration.

2. The method of claim 1, wherein the step of exposing the selected oat fraction includes exposing oat flour.

3. The method of claim 2, wherein the step of exposing includes exposing the oat flour to from 2 to 10 KJ/g of infrared energy.

4. The method of claim 2, wherein the step of exposing includes exposing the oat flour to up to 10 KJ/g of infrared energy.

5. The method of claim 2, wherein the step of exposing includes exposing the oat flour to greater than 2 KJ/g of infrared energy.

6. The method of claim 1, wherein the step of exposing comprises exposing oat hulls.

7. The method of claim 6, wherein the step of exposing to infrared energy comprises exposing the oat hulls to from 2 to 10 KJ/g.

8. The method of claim 6, wherein the step of exposing includes exposing the oat hulls to up to 10 KJ/g of infrared energy.

9. The method of claim 6, wherein the step of exposing includes exposing the oat hulls to greater than 2 KJ/g of infrared energy.

10. The method of claim 1, wherein the oat fraction comprises oat trichomes.

11. The method of claim 10, wherein the step of exposing to infrared energy comprises exposing the oat trichomes to from 2 to 10 KJ/g.

12. The method of claim 10, wherein the step of exposing includes exposing the oat trichomes to up to 10 KJ/g of infrared energy.

13. The method of claim 10, wherein the step of exposing includes exposing the oat trichomes to greater than 2 KJ/g of infrared energy.

14. The method of claim 1, wherein the step of exposing the oat fraction further includes exposing the oat fraction while the oat fractions are undergoing flaking.

15. The method of claim 1, wherein the step of exposing the oat fraction further includes exposing the oat fraction while the oat fractions are undergoing kilning.

16. The method of claim 1, wherein the step of exposing the oat fraction further includes exposing the oat fraction between one oat processing step and another.

17. The method of claim 1, wherein the step of exposing the oat fraction further includes exposing the oat fraction prior to packaging.

18. The method of claim 1, wherein the step of exposing to infrared energy is continued to increase the concentration of total Avenanthramides of the selected oat fraction by from 10 to 70 wt. % above the concentration of total Avenanthramides of the selected oat fraction prior to the step of exposing to infrared energy.

19. The method of claim 1, wherein the step of exposing to infrared energy is continued to increase the concentration of total Avenanthramides of the oat fraction by from 5 to 20 wt. % above the concentration of total Avenanthramides of the selected oat fraction prior to the step of exposing to infrared energy.

* * * * *